:::
United States Patent [19]

Tsou

[11] Patent Number: 5,176,678
[45] Date of Patent: Jan. 5, 1993

[54] ORTHOPAEDIC DEVICE WITH ANGULARLY ADJUSTABLE ANCHOR ATTACHMENTS TO THE VERTEBRAE

[76] Inventor: Paul M. Tsou, 526 Adelaide Dr., Santa Monica, Calif. 90402

[21] Appl. No.: 669,650

[22] Filed: Mar. 14, 1991

[51] Int. Cl.⁵ ............................................. A61F 5/01
[52] U.S. Cl. .................................... 606/61; 606/60; 606/53
[58] Field of Search ................. 606/53, 54, 59, 60, 606/61, 72, 73, 86, 105

[56] References Cited

U.S. PATENT DOCUMENTS

| | | | |
|---|---|---|---|
| 4,361,141 | 11/1982 | Tanner | 128/69 |
| 4,433,676 | 2/1984 | Bobechko | 606/61 |
| 4,655,199 | 4/1987 | Steffee | 606/61 X |
| 4,805,602 | 2/1989 | Puno et al. | 128/69 |
| 5,007,909 | 4/1991 | Rogozinski | 606/61 |
| 5,053,034 | 10/1991 | Olerud | 606/54 X |

FOREIGN PATENT DOCUMENTS

2131300  6/1984  United Kingdom ............... 606/105

Primary Examiner—Robert A. Hafer
Assistant Examiner—Sam Rimell
Attorney, Agent, or Firm—B. F. Spencer

[57] ABSTRACT

An orthopaedic device is disclosed for mechanical intercoupling between selected vertebrae of the human spine and an elongated surgical rod. The device includes a block-shaped member having upper and lower surfaces, front and rear surfaces, and left and right side surfaces. A central cylindrical bore extends through the block-shaped member between the upper and lower surfaces. A longitudinal slot extends between the upper and lower surfaces, and from the front and one side surface of the block member into the central bore. The central bore and longitudinal slot serve as a yoke into which a section of the surgical rod may be placed, the width of the slot being slightly larger than the diameter of the rod. A short, hollow, cylindrical sleeve member, with internal diameter slightly larger than the diameter of the rod, is adapted for slidable movement over the rod and into the central bore of the block-shaped member to provide capture of the surgical rod. A recessed, hollow socket extends part way into the block-shaped member between the central bore and the rear surface of the block-shaped member. An aperture extends from the bottom of the socket out through the rear surface. The recessed socket serves to retain the support and head of an angularly adjustable, removable anchor attachment member, i.e., a hook member or surgical screw, the hook member being designed for providing limited angular movement within the socket in a plane perpendicular to the axis of the surgical rod.

6 Claims, 1 Drawing Sheet

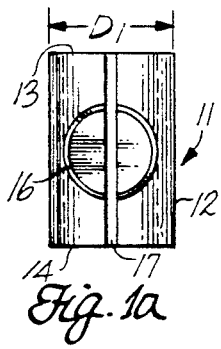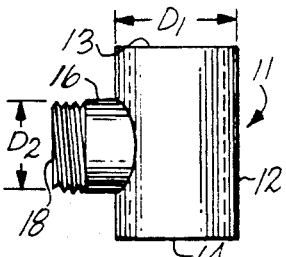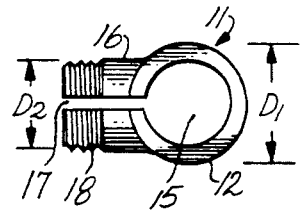
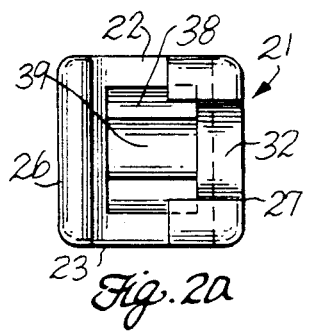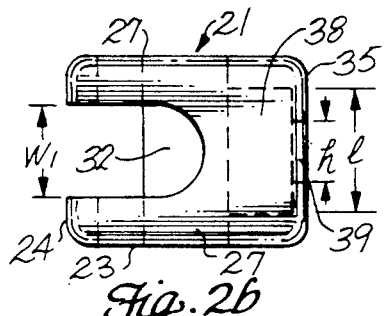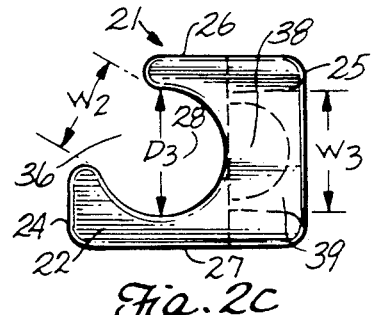
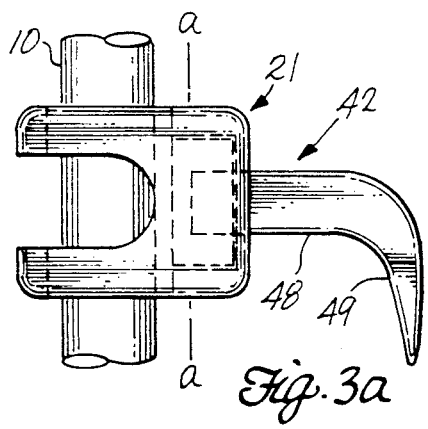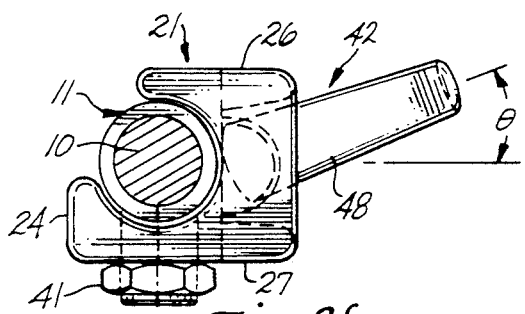
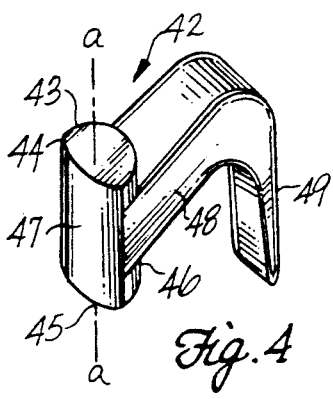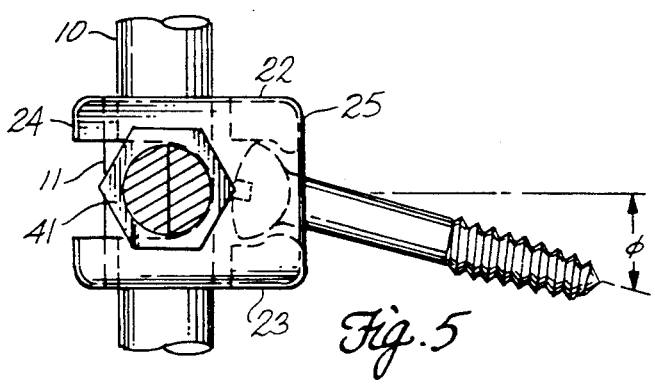

ORTHOPAEDIC DEVICE WITH ANGULARLY ADJUSTABLE ANCHOR ATTACHMENTS TO THE VERTEBRAE

BACKGROUND OF THE INVENTION

The present invention relates to orthopaedic devices, and, in particular, to devices providing improved alignment and coupling between the vertebrae of the spine and a longitudinally extending surgical rod. This invention is related to application Ser. No. 669,651, now U.S. Pat. No. 5,122,131 entitled "Orthopaedic Device for Mechanical Coupling to a Surgical Rod" and filed concurrently herewith.

The use of longitudinally extending surgical rods in the treatment of the diseases of the spine, such as scoliosis, kyphosis, and instability, is well-kmown in the medical arts. Such rods achieve rigid spinal fixation when mechanically coupled to bone anchor attachments, such as hooks or screws. These surgical rods are used, generally, in pairs placed on the posterior surface of the left and right sides of the lamina of the human spine.

One widely used anchor attachment is the conventional orthopaedic hook having a block-shaped head portion, with a central, cylindrical bore therethrough, and a hook portion. The bore of the conventional orthopaedic hook is adapted to receive the surgical rod, and the head is slidably positioned over the surface of the surgical rod to the selected vertebra for attachment. The hook may have a variety of different shapes, lengths and openings to accommodate the specific vertebra to which it is to be anchored. With the hook portion properly anchored, the conventional orthopaedic hook is locked to the surgical rod either by ratchet or by one or more setscrews located within the block-shaped head.

Another anchor attachment is a special orthopaedic screw having a block-shaped head with cylindrical bore therethrough. The screw, when its threaded end is attached to the selected anatomical site, is adapted for receiving and passing the elongated surgical rod through its cylindrical bore. Since the shank and threaded end of the screw extends perpendicularly with respect to the axis of the bore, once the screw has been anchored the position of the head, with its cylindrical bore, is fixed with respect to the spine of the patient.

If the nature of the disease of the spine should require the attachment of a number of orthopaedic screws at spaced-apart anatomical sites, it will be appreciated that manual insertion of an elongated surgical rod through the bores of the several spaced-apart orthopaedic screws is surgically difficult. The alignment of the axis of the bore in the head of each screw must, of necessity, bear some relationship to a common axis related to the axis of the surgical rod, which rod must be inserted through the several bores. Since the nature of the surgical operation places the surgical rod under stress, as by resisting deforming forces of the spine, it will be appreciated that proper positioning of the heads and alignment of the bores of the several anchor attachment members is of paramount concern.

With the conventional orthopaedic hook, it is frequently found that when the hook is inserted over, or under, the selected vertebra to which it is to be anchored, the axis of the bore through the head of the hook does not fall into the axial alignment desired. In such case, the hook must either be altered or replaced with another of different length, shape or opening.

Recognizing that the surgical rods, with their anchor attachments, are installed during open-back surgery, while the patient is under anesthesia, it is important for the orthopaedic surgeon to have available for immediate use anchor attachments that are easily positioned and aligned between the vertebrae and the surgical rods to which they are to be secured.

The present invention introduces an orthopaedic device having angularly adjustable anchor attachment members for mechanical intercoupling between selected vertebrae of the spine and a surgical rod. The device includes a block-shaped member having a central cylindrical bore within which the surgical rod is to be positioned and secured. The block-shaped member includes a recessed, hollow socket extending part way into the block-shaped member between the central bore and the rear surface thereof. An aperture extends from the bottom of the recessed, hollow socket out through the rear surface of the block-shaped member. The recessed, hollow socket serves to retain and support the head of an angularly adjustable and removable anchor attachment member. One angularly adjustable and removable attachment is the novel orthopaedic hook member of the invention, which hook member includes a short, rod-shaped cylindrical head portion, a shank portion, and a hook portion. The shank and hook portion is designed for insertion through the recessed, hollow socket and out through the aperture. The short, rod-shaped cylindrical head portion is designed to seat within the recessed, hollow socket. The novel orthopaedic hook member is adapted for limited angular movement within the recessed, hollow socket in a plane perpendicular to the axis of the central bore of the block-shaped member. This angular movement is about the axis of the short, rod-shaped cylindrical head portion, which axis is spaced apart from and parallel to the axis of the central bore. The "ball-headed" surgical screw is another removable anchor attachment for use with the invention. The recessed, hollow socket and the aperture pass the shank and threaded end of the screw while the hollow socket retains and seats the ball head of the screw in a "ball and socket" arrangement.

Accordingly, a principal object of the present invention is to provide an orthopaedic device capable of achieving improved mechanical alignment and coupling between a selected vertebra of the human spine and a longitudinally extending surgical rod.

Another object is to provide an orthopaedic device having an angularly adjustable anchor attachment member for providing improved alignment with and attachment to a selected vertebra of the spine.

Yet another object is to provide an improved orthopaedic hook member providing limited angular movement in a plane perpendicular to the axis of a longitudinally extending surgical rod to which the hook member is to be coupled.

Still another object is to provide an orthopaedic device, modular in design, adapted for receiving and supporting any one of a number of removable anchor attachment members of different shapes, openings and lengths.

An additional object is to provide an orthopaedic hook adapted for limited angular positioning about an axis spaced apart from and parallel to the axis of a surgical rod to which the orthopaedic hook is to be coupled.

A further object is to provide an orthopaedic device which, after attachment to a selected vertebra, is easier to align and to attach to an elongated surgical rod.

The above objects of and the brief introduction to the present invention will be more fully understood, and further objects and advantages will become more apparent, from a study of the following detailed description in connection with the drawing.

BRIEF DESCRIPTION OF THE DRAWING

FIGS. 1a, 1b and 1c are enlarged illustrations of the front, side, and top, respectively, of a T-shaped, hollow sleeve member for slidable positioning over the surface of a surgical rod and into a cylindrical bore of the orthopaedic device of the invention for securing and locking the orthopaedic device to the surgical rod.

FIGS. 2a, 2b and 2c are enlarged views of the front, side and top, respectively, of the orthopaedic device of the invention.

FIG. 3a is an enlarged view of the side of the orthopaedic device with the angularly adjustable and removable hook member of the invention.

FIG. 3b is an enlarged top view of the orthopaedic device and hook member of FIG. 3a shown secured and locked to a surgical rod by means of the T-shaped sleeve member of FIGS. 1a, 1b and 1c.

FIG. 4 is an enlarged perspective view of the novel, angularly adjustable and removable hook member of FIGS. 3a and 3b.

FIG. 5 is an enlarged side view of the orthopaedic device secured to a surgical rod, the device retaining and seating the head of a "ball-headed" surgical screw within the recessed, hollow socket in a swivel-like manner.

DESCRIPTION OF THE INVENTION

Referring to FIGS. 1a, 1b and 1c of the drawing, a T-shaped member 11 having a first hollow cylindrical sleeve section 12 with upper and lower ends 13, 14, respectively, is shown for use in connection with the present invention. Hollow cylindrical sleeve section 12 includes bore 15 extending between ends 13 and 14. Bore 15 is dimensioned to slidably receive and pass a longitudinally extendimg surgical rod.

A second short cylindrical rod section 16, located midway between upper and lower ends 13 and 14, extends perpendicularly from hollow cylindrical sleeve section 12 and is integral therewith, as seen in FIG. 1b. The outer diameter $D_1$ of hollow cylindrical sleeve section 12 is larger than the diameter $D_2$ of cylindrical rod section 16. The diameter $D_2$ of cylindrical rod section 16 is approximately equal to the diameter of the surgical rod for which the orthopaedic device of this invention is to be used.

As can be seen in FIGS. 1a and 1c, a narrow slot 17 extends through the center of cylindrical rod section 16 and through the wall of hollow cylindrical sleeve section 12. Narrow slot 17 extends parallel to the axis of hollow sleeve section 12 from upper surface 13 to lower surface 14 and bisects cylindrical rod section 16. The width of narrow slot 17 is sufficient to permit T-shaped member 11 to be clamped upon the cylindrical surface of the surgical rod when a squeezing force exists between the bisected halves of cylindrical rod section 16, thereby reducing the gap in slot 17.

The squeezing force needed to achieve the desired clamping upon the surgical rod is provided by the threaded end 18 of bisected, cylindrical rod section 16. It is preferred that threaded end 18 be slightly tapered, as in pipe threads, to enable a conventional locking nut engaging threaded end 18 to gradually reduce the gap in slot 17 as the locking nut advances. The T-shaped member 11 in FIGS. 1a, 1b and 1c is the same as shown and described in copending application Ser. No. 669,651, now U.S. Pat. No. 5,122,131.

Referring to FIGS. 2a, 2b and 2c, the improved orthopaedic device of the invention includes block-shaped member 21 having upper and lower surfaces 22, 23, front and rear surfaces 24, 25, and having left-side and right-side surfaces 26, 27, respectively. A cylindrical bore 28 extends through the central portion of block-shaped member 21 between upper and lower surfaces 22, 23, as best seen in FIG. 2c. The diameter $D_3$ of cylindrical bore 28 is slightly larger than the outer diameter $D_1$ of hollow cylindrical sleeve section 12 of T-shaped member 11, as will be explained hereinbelow.

A U-shaped cutout 32 in the right side 27 of block-shaped member 21 extends from the flat surface of the right side 27 through block-shaped member 21 into central bore 28. The open end of U-shaped cutout 32 extends to front surface 24, as best seen in FIG. 2b. The width $W_1$ of U-shaped cutout 32 is slightly larger than the diameter $D_2$ of cylindrical rod section 16 of T-shaped member 21, as will be further explained hereinbelow.

A longitudinally extending slot 36 of width $W_2$ extends from a portion of front surface 24 and a portion of left side 26 through block-shaped member 21 into central bore 28, as best seen in FIG. 3c. Slot 36, parallel to the axis of bore 28, extends between the upper and lower surfaces 22, 23 of the block-shaped member 21. The width $W_2$ of slot 36 is substantially the same as the width $W_1$ of U-shaped cutout 32, but is less than the diameter $D_3$ of central bore 28, as can be seen in FIG. 2c.

A recessed, hollow socket 38 extends part way into block-shaped member 21 between central bore 28 and rear surface 25, as best seen in FIG. 2c. The bottom of recessed, hollow socket 38, nearest rear surface 25, is cylindrically shaped with its axis a—a extending in a direction parallel to the axis of central bore 28. The diameter of the cylindrically shaped bottom surface is approximately the same as that of the surgical rod to be used with the invention.

The length l of the recessed, hollow cylindrically shaped socket is less than the distance between upper and lower surfaces 22 and 23, as seen in FIG. 2b, and this length is approximately the same as the diameter $D_3$ of cylindrical bore 28.

An aperture 39 extends from the cylindrical bottom of recessed, hollow socket 38 through block-shaped member 21 and out through rear surface 25, as seen in FIGS. 2b and 2c. Aperture 39 is rectangular in shape, as seen in FIGS. 2a and 2b, and has a height h, as seen in FIG. 2b, and a width $W_3$, as seen in FIG. 2c.

The recessed, hollow socket 38, together with aperture 39 of block-shaped member 21 of FIGS. 2a, 2b and 2c, serves to retain and support an angularly adjustable and removable anchor attachment member, as will be explained in connection with FIGS. 3a and 3b.

FIGS. 3a and 3b illustrate the improved orthopaedic device of the invention supporting the novel orthopaedic hook member 42 for limited angular movement about an axis parallel to and spaced apart from the axis of central bore 28, the axis of central bore 28 coinciding with the axis of the surgical rod to which the improved orthopaedic device is to be mechanically coupled. Orthopaedic hook member 42, illustrated in perspective in FIG. 4, includes a short, rod-shaped head portion 43 having spaced-apart upper and lower ends 44, 45. The rear surface 46 of rod-shaped head portion 43 is cylindrically shaped. The axis a—a of cylindrically shaped rear surface 46 extends through rod-shaped head portion 46. The front surface 47 of rod-shaped head portion 43 has an oval shape, as viewed in FIG. 3b and FIG. 4, which shape extends between upper and lower ends 44, 45.

A rectangularly shaped shank member 48 has one end integrally attached to rear surface 46 of rod-shaped head portion 43 at a position approximately midway between upper and lower ends 44, 45. Shank portion 48 extends outwardly from rod-shaped head portion 43 and lies, generally, in a plane substantially perpendicular to the axis a—a extending through rod-shaped head portion 43.

A curved hook portion 49 is integrally attached to the other end of shank portion 48 and extends in a generally downward direction. Hook portion 49 may have any of the shapes, openings or lengths of conventional orthopaedic hooks.

The hook member 42 is shown positioned and seated within recessed, hollow cylindrical socket 38 of block-shaped member 21 in FIG. 3b for limited angular movement about axis a—a. The degree of angular movement of hook member 42 within hollow socket 38 is governed, in part, by the width $W_3$ of rectangular aperture 39, and may be as much as plus or minus twenty degrees.

The manual procedure for mechanically coupling the orthopaedic device of the invention, along with its novel orthopaedic hook, to a surgical rod, as illustrated in FIG. 3b, is identical to the procedure shown and described in copending application Ser. No. 669,651. T-shaped member 11 is first slidably positioned on surgical rod 10. The surgical rod is then placed within bore 28 and the T-shaped member 11 slidably positioned over the surface of the surgical rod and into central bore 28. The bisected, threaded rod section 16 of T-shaped member 11 is then positioned into U-shaped cutout 32 by rotating T-shaped member 11 about the axis of surgical rod 10. A locking nut 41, threadably engaged on threaded end 18 serves to clamp the surgical rod and secure the orthopaedic assembly to surgical rod 10.

FIG. 5 is a side view of an embodiment of the orthopaedic device of the invention retaining and seating the head of a "ball-headed" surgical screw for limited angular movement in a swivel-like manner. The recessed, hollow socket extending part way into the block-shaped member has a hemispherical-shaped bottom surface. The aperture extending from the bottom of the recessed, hollow hemispherical-shaped socket and out through the rear surface is circular in shape. The diameter of the circular aperture is somewhat larger than the diameter of the shank of the "ball-headed" surgical screw, and is smaller than the diameter of the head of the screw. The diameter of the circular aperture, relative to the diameter of the shank of the surgical screw, governs, in part, the degree of angular movement of the screw.

The embodiment of the invention illustrated in FIG. 5 is shown secured to surgical rod 10 by means of T-shaped member 11 and locking nut 41. The manual procedure for achieving this secure locking is the same as described above in connection with FIG. 3b and as shown and described in copending Application Ser. No. 669,651.

It should be noted that the top surface of the "ball-headed" surgical screw does not have to be spherical in shape. Preferably, it is oval in shape, as in the conventional oval-headed machine screw, as illustrated in FIG. 5. This enables the recessed, hollow, hemispherical socket to have a somewhat smaller depth than ordinarily would be the case.

The embodiments of the invention illustrated in FIGS. 3b and FIG. 5 show the orthopaedic device secured to a surgical rod as the surgical rod would be positioned on the right side of the human spine, thus placing the locking nut on the opposite side of the surgical rod from the spine, for easy access by a hexagonal wrench.

Due to the symmetry of the orthopaedic device of the invention, it is apparent that the device can be inverted from the positions shown in FIG. 3b and in FIG. 5 to allow the device to be employed on the left side of the spine of the patient. The length of short, rod-shaped head portion 43 of hook member 42, between upper and lower ends 44, 45, is slightly less than the length 1 of rectangular aperture 39, as seen in FIG. 3a, facilitating removal and inversion of hook member 42.

The orthopaedic device of the invention is not limited to the embodiments disclosed. It is believed apparent, for example, that the recessed, hollow socket 38 may be shaped to retain a flat-headed machine screw to enable the block-shaped member 21 to be rigidly attached to additional orthopaedic implants. For example, a "ball-headed" machine screw may be employed for threaded attachment to an orthopaedic plate member.

Since many changes may be made in the above-described device and many different embodiments of this invention could be made without departing from the scope thereof, it is intended that all matter contained in the above description or shown in the accompanying drawings shall be interpreted as illustrative and not in a limiting sense.

What is claimed is:

1. An orthopaedic device adapted for mechanical intercoupling between selected vertebrae of the human spine and a longitudinally extending surgical rod, comprising in combination:

(a) a T-shaped member having a hollow, cylindrical sleeve section with a cylindrical bore extending therethrough, said T-shaped member having a cylindrical rod section extending perpendicularly from said hollow, cylindrical sleeve section, said hollow, cylindrical sleeve section having a first outer diameter, said cylindrical rod section having a second outer diameter less than the first outer diameter of said hollow, cylindrical sleeve section, the bore extending through said hollow, cylindrical sleeve section having a diameter sufficient to receive and pass the longitudinally extending surgical rod;

(b) a first narrow slot extending through the center of said cylindrical rod section bisecting said cylindrical rod section, said first narrow slot extending through a wall portion of said hollow, cylindrical sleeve section into the cylindrical bore, said first narrow slot lying in a plane defined by the axes of said hollow, cylindrical sleeve section and said cylindrical rod section, the axis of said hollow, cylindrical sleeve section being substantially perperdicular to the axis of said bisected cylindrical rod section;

(c) a block-shaped member adapted for slidably receiving said hollow, cylindrical sleeve section of said T-shaped member, said block-shaped member having upper and lower surfaces spaced apart, front and rear surfaces spaced apart, and left and right flat side surfaces spaced apart;

(d) a centrally located cylindrical bore extending through said block-shaped member between said upper and lower surfaces, the central bore of said block-shaped member having a diameter slightly larger than the outer diameter of said hollow, cylindrical sleeve section of said T-shaped member;

(e) a U-shaped cutout extending from one flat side surface of said block-shaped member and through said block-shaped member into said central bore, said U-shaped cutout having a width slightly larger than the outer diameter of the bisected, cylindrical rod section of said T-shaped member;

(f) a longitudinal slot extending between the upper and lower surfaces of said block-shaped member, said longitudinal slot extending from the front surface of said block-shaped member into said central bore, the width of said longitudinal slot being slightly larger than the diameter of the longitudinally extending surgical rod and being slightly smaller than the diameter of said central bore;

(g) a recessed, hollow socket extending part way into said block-shaped member from said central bore toward said rear surface, said recessed, hollow socket being located approximately midway between said upper and lower surfaces;

(h) an aperture extending from the bottom of said recessed hollow socket and out through said block-shaped member to said rear surface, said recessed, hollow socket being adapted for retaining and supporting the head of an angularly adjustable anchor attachment member, the angularly adjustable anchor attachment member including a portion passing out through said aperture for mechanical attachment to a selected vertebra; and (i) means adapted to be attached to said bisected cylindrical rod section, when said T-shaped member is positioned within said central bore of said block-shaped member and said bisected cylindrical rod section is positioned within said U-shaped cutout, for applying a force tending to squeeze the bisected cylindrical rod section of said T-shaped member, thereby reducing the gap in said first narrow slot to provide a clamping force upon a surgical rod within said hollow, cylindrical sleeve section of said T-shaped member, said means further applying a force against said one flat side surface of said block-shaped member for securing said T-shaped member within said block-shaped member.

2. The orthopaedic device as defined by claim 1 wherein said longitudinal slot, extending between said upper and lower surfaces of said block-shaped member, further extends from the front surface and a portion of one side surface of said block-shaped member into said central bore.

3. The orthopaedic devices as defined by claim 1 wherein said recessed, hollow socket, extending part way into said block-shaped member between said central bore and the rear surface of said block-shaped member, has a cylindrically shaped bottom surface, the axis of said cylindrically shaped bottom surface being substantially parallel to the axis of said central bore, and wherein said aperture, extending from the bottom of said recessed, hollow socket and out through the rear surface of said block-shaped member, is rectangular in shape.

4. The orthopaedic device as defined by claim 1 wherein said recessed, hollow socket, extending part way into said block-shaped member between said central bore and the rear surface of said block-shaped member, has a hemispherical-shaped bottom surface, and wherein said aperture, extending from the bottom of said recessed, hollow socket and out through the rear surface of said block-shaped member, is circular in shape, the diameter of said circular-shaped aperture being less than the diameter of said hemispherical-shaped bottom surface of said recessed, hollow socket.

5. The orthopaedic device as defined by claim 1 wherein said recessed, hollow socket, extending part way into said block-shaped member between said central bore and the rear surface of said block-shaped member, has a cylindrically shaped bottom surface, the axis of said cylindrically shaped bottom surface being substantially parallel to the axis of said central bore, and wherein said aperture, extending from the bottom of said recessed, hollow socket and out through the rear surface of said block-shaped member, is rectangular in shape, said recessed, hollow socket with cylindrically shaped bottom surface being adapted for receiving and supporting the head of a removable hook member for limited angular movement about an axis parallel to and spaced apart from the axis of said central bore, said removable hook member having a rectangular-shaped shank member having one end integrally attached to the rear surface of the head of said hook member, a portion of said rectangular-shaped shank member extending out through said rectangular-shaped aperture, the end of said rectangular-shaped shank member having a curved hook adapted for attachment to a selected vertebra.

6. The orthopaedic device as defined by claim 1 wherein said recessed, hollow socket, extending part way into said block-shaped member between said central bore and the rear surface of said block-shaped member, has a hemispherical-shaped bottom surface, and wherein said aperture, extending from the bottom of said recessed, hollow socket and out through the rear surface of said block-shaped member, is circular in shape, the diameter of said circular-shaped aperture being less than the diameter of said hemispherical-shaped bottom surface of said recessed, hollow socket, said recessed, hollow socket with hemispherical-shaped bottom surface being adapted for receiving and supporting the head of a removable surgical screw for limited angular movement about the axis of said surgical screw, said removable surgical screw having a shank portion extending out through said circular aperture, the diameter of said circular aperture being somewhat larger than the diameter of said shank portion, said surgical screw having a threaded end for attachment to a selected vertebra.

* * * * *